US011116881B2

(12) United States Patent
Hahne et al.

(10) Patent No.: US 11,116,881 B2
(45) Date of Patent: Sep. 14, 2021

(54) FILTRATION SYSTEM AND PROCESS FOR PERITONEAL DIALYSIS

(71) Applicant: Cook Medical Technologies LLC, Bloomington, IN (US)

(72) Inventors: Kalub Hahne, West Lafayette, IN (US); Keith Milner, West Lafayette, IN (US); Duane Blatter, Salt Lake City, UT (US); Andrew Isch, West Lafayette, IN (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 0 days.

(21) Appl. No.: 15/606,515

(22) Filed: May 26, 2017

(65) Prior Publication Data

US 2017/0340794 A1 Nov. 30, 2017

Related U.S. Application Data

(60) Provisional application No. 62/342,821, filed on May 27, 2016.

(51) Int. Cl.
*A61M 1/28* (2006.01)
*A61M 1/16* (2006.01)
(Continued)

(52) U.S. Cl.
CPC ............. *A61M 1/287* (2013.01); *A61K 31/19* (2013.01); *A61K 31/718* (2013.01); *A61K 33/00* (2013.01);
(Continued)

(58) Field of Classification Search
CPC ........ A61M 1/287; A61M 1/284; A61M 1/28; A61M 1/1696; A61M 1/3482;
(Continued)

(56) References Cited

U.S. PATENT DOCUMENTS 4,338,190 A * 7/1982 Kraus ..................... A61M 1/28
210/195.2
4,976,683 A 12/1990 Gauthier et al.
(Continued)

FOREIGN PATENT DOCUMENTS

WO WO 2000/030701 A1 6/2000
WO WO 2006/088419 A2 8/2006
(Continued)

OTHER PUBLICATIONS

Frampton et al, "Icodextrin: a review of its use in peritoneal dialysis", Drugs 2003; 63(19); 2079-105 (abstract).*
(Continued)

*Primary Examiner* — Krishnan S Menon
(74) *Attorney, Agent, or Firm* — Woodard, Emhardt Et Al.

(57) ABSTRACT

Described are peritoneal dialysis systems and methods that involve the use of crossflow filtration of a used dialysate withdrawn from the peritoneal space of a patient. The filtration forms a retentate containing amounts of an osmotic agent and a permeate containing amounts of water and nitrogen-containing waste products of the patient. The retentate, or a fraction thereof, can be returned to the peritoneal space of the patient to return osmotic agent to the patient. The permeate, or a fraction thereof, can be discarded to discard nitrogen-containing waste products of the patient.

19 Claims, 1 Drawing Sheet

(51) Int. Cl.
    *A61M 1/34*     (2006.01)
    *A61K 31/19*     (2006.01)
    *A61K 31/718*     (2006.01)
    *A61K 33/00*     (2006.01)
    *A61K 33/06*     (2006.01)

(52) U.S. Cl.
    CPC .......... *A61K 33/06* (2013.01); *A61M 1/1696* (2013.01); *A61M 1/28* (2013.01); *A61M 1/284* (2014.02); *A61M 1/285* (2013.01); *A61M 1/3482* (2014.02); *A61M 2202/0486* (2013.01); *A61M 2205/75* (2013.01); *A61M 2205/8206* (2013.01)

(58) Field of Classification Search
    CPC .......... A61M 1/285; A61M 2202/0486; A61M 2205/75; A61M 2205/8206; A61K 31/19; A61K 31/718; A61K 33/00; A61K 33/06
    See application file for complete search history.

(56) References Cited

U.S. PATENT DOCUMENTS

| | | |
|---|---|---|
| 5,944,684 A | 8/1999 | Roberts et al. |
| 6,077,836 A * | 6/2000 | Milner .................. A61K 31/718 514/54 |
| 8,282,828 B2 | 10/2012 | Walenaas |
| 8,349,813 B2 | 1/2013 | Johnson et al. |
| 8,404,091 B2 | 3/2013 | Ding et al. |
| 8,777,892 B2 | 7/2014 | Sandford et al. |
| 8,882,700 B2 | 11/2014 | Chapman et al. |
| 2006/0241543 A1 | 10/2006 | Gura |
| 2009/0239238 A1 | 9/2009 | Wang et al. |
| 2009/0239819 A1 | 9/2009 | Wang et al. |
| 2013/0226065 A1 | 8/2013 | Wolff et al. |
| 2014/0158623 A1 | 6/2014 | Pudil et al. |
| 2014/0217028 A1 | 8/2014 | Pudil et al. |
| 2014/0251908 A1 | 9/2014 | Ding et al. |
| 2014/0276376 A1 | 9/2014 | Rohde et al. |
| 2015/0005699 A1 | 1/2015 | Burbank et al. |
| 2015/0021268 A1 | 1/2015 | Ding et al. |
| 2017/0281847 A1 * | 10/2017 | Manda ................ A61M 1/1686 |

FOREIGN PATENT DOCUMENTS

| | | |
|---|---|---|
| WO | WO 2008/020801 A1 | 2/2008 |
| WO | WO 2014/099631 A1 | 6/2014 |
| WO | WO 2016/191728 A1 | 12/2016 |

OTHER PUBLICATIONS

European Patent Application No. 17173091.4 Extended European Search Report dated Oct. 12, 2017. 11 pages.

* cited by examiner

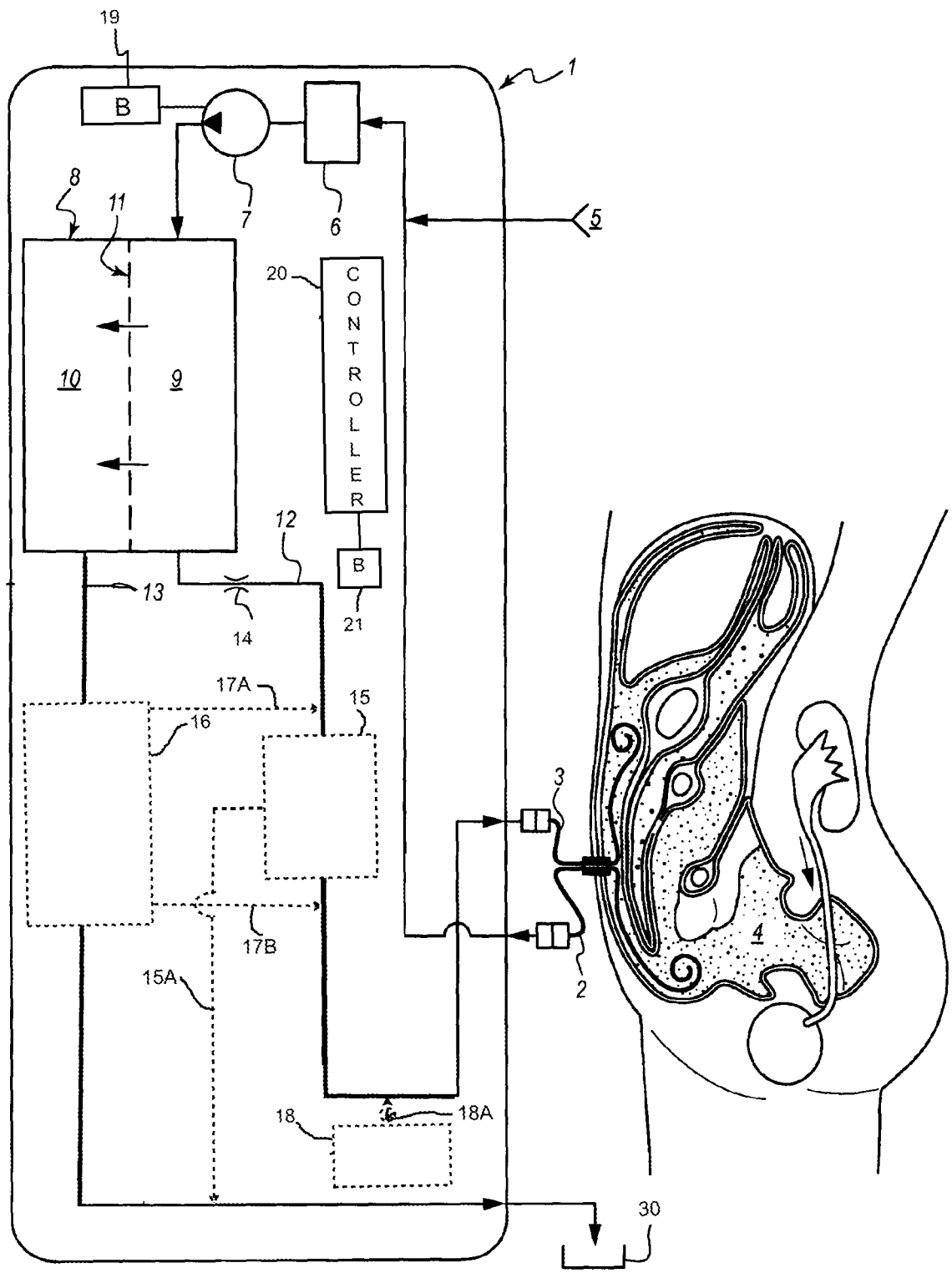

FILTRATION SYSTEM AND PROCESS FOR PERITONEAL DIALYSIS

REFERENCE TO RELATED APPLICATION

This application claims the benefit of U.S. Provisional Application No. 62/342,821, filed May 27, 2016, which is hereby incorporated by reference.

BACKGROUND

For patients with chronic kidney disease who require renal replacement therapy, Peritoneal Dialysis (PD) has been shown to have significant advantages over hemodialysis. These advantages include lower overall costs, fewer hospitalizations and lower patient mortality. In addition, the process of peritoneal dialysis has been made relatively simple and most patients can learn the necessary skills. PD gives the patient greater flexibility in planning when to do dialysis.

Most patients receiving PD are treated with Automated Peritoneal Dialysis (APD). APD is a protocol of daily (usually nightly) treatment utilizing an automated pump. Typically multiple fill-drain cycles are programmed into the machine and occur automatically while the patient sleeps. Typically 12 to 15 liters are pumped into and out of the peritoneal space in 2 to 3 liter cycles with a specified dwell time between infusion and removal. The effluent is discarded into a drain.

Another implementation of PD is referred to Continuous Ambulatory Peritoneal Dialysis (CAPD). Patients receiving renal replacement therapy with CAPD manually infuse a defined amount of dialysate fluid into the peritoneal space at several times during the day, leaving the fluid for the dwell time and then manually draining into the drain bag.

In spite of its advantages, PD remains underutilized, particularly in the U.S. Only approximately 10% of kidney failure patients in the U.S. use PD for renal replacement. The limitations inherent to current implementations of PD contribute significantly to the underutilization. These limitations include:

The externalized catheter is inconvenient, causing limitations on showering, bathing and other activities of daily living.
  There is a significant continuous risk of catheter tract infections and peritonitis and its complications.
  Rapid transport of glucose across the peritoneal membrane in some patients renders PD ineffectual
  The use of glucose based PD fluids that complicate blood sugar control in diabetic patients and cause weight gain in nearly all PD patients.
  The complexity of the PD system, though moderate, can be intimidating for some patients and helpers.
  While doing APD the patient is tethered to a bulky machine which limits mobility.
  Large volumes of PD fluid must be delivered to and stored by the patient.

Various embodiments disclosed herein can eliminate or ameliorate one or more of the foregoing disadvantages with prior art systems. Various embodiments make PD easier to use and applicable to a larger percentage of chronic renal failure patients.

SUMMARY

In certain aspects, provided are unique systems and methods for conducting peritoneal dialysis or regenerating a used dialysate solution. The methods and systems include filtering a used dialysate recovered from a peritoneal space of a patient to form a first retentate containing amounts of an osmotic agent of the dialysate solution and a permeate containing urea, creatinine and potentially other waste products from the patient. Accordingly, in some embodiments herein, provided are methods for processing a used peritoneal dialysate recovered from a peritoneal space of a patient, the used dialysate containing an osmotic agent. The methods include filtering the used dialysate under crossflow filtration conditions across a membrane. The membrane can have a molecular weight cutoff lower than a weight average molecular weight of the osmotic agent. The filtering generates a retentate containing at least 50%, at least 60%, more preferably at least 70%, by weight of the osmotic agent present in the used dialysate. The retentate also has a first concentration of urea from the used dialysate, a first concentration of creatinine from the used dialysate, and a first concentration of sodium from the used dialysate. The filtering also generates a permeate containing a second concentration of urea from the used dialysate, a second concentration of creatinine from the used dialysate, and a second concentration of sodium from the used dialysate.

In other embodiments, provided are peritoneal dialysis apparatuses that include an uptake catheter for removing a peritoneal dialysis ultrafiltrate from a peritoneal space of a patient containing an osmotic agent, water, and nitrogen-containing waste products of metabolism of the patient; optionally a filter arranged to filter particles from the peritoneal dialysis ultrafiltrate to form a pre-filtered peritoneal dialysis ultrafiltrate; a filter arranged for crossflow filtration of the used dialysate across a membrane having a molecular weight cutoff lower than a weight average molecular weight of the osmotic agent; and a pump for pumping the used dialysate through the filter. The filter and pump are arranged to generate, when the pump is used to pump the used dialysate through the filter, a retentate and a permeate. The retentate contains at least 50%, at least 60%, more preferably at least 70%, by weight of the osmotic agent present in the used dialysate. The retentate also has a first concentration of urea from the used dialysate, a first concentration of creatinine from the used dialysate, and a first concentration of sodium from the used dialysate. The permeate contains a second concentration of urea from the used dialysate, a second concentration of creatinine from the used dialysate, and a second concentration of sodium from the used dialysate. The system can also include a return catheter for returning the permeate, or components thereof, to the peritoneal space of the patient. The return catheter can be the same catheter as the uptake catheter, or a different catheter than the uptake catheter.

Additional embodiments of peritoneal dialysis or peritoneal dialysate processing methods and apparatuses, as well as features and advantages attendant thereto, will be apparent from the descriptions herein.

BRIEF DESCRIPTION OF THE DRAWINGS

FIG. 1 is a schematic representation of one embodiment of a system for reconstitution of peritoneal dialysis fluid and its connections to the peritoneal space of a patient.

DETAILED DESCRIPTION

For the purpose of promoting an understanding of the principles of the invention, reference will now be made to embodiments, some of which are illustrated with reference to the drawings, and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates. Additionally, in the detailed description below, numerous alternatives are given for various features related to the composition or size of materials, or to modes of carrying out methods. It will be understood that each such disclosed alternative, or combinations of such disclosed alternatives, can be combined with the more generalized features discussed in the Summary above, or set forth in the Listing of Certain Embodiments below, to provide additional disclosed embodiments herein.

As disclosed above, aspects of the present disclosure relate to methods and systems for processing a dialysate removed from a peritoneal space of a patient, for example as part of a peritoneal dialysis (PD) process. The dialysate contains an amount of an osmotic agent, for example a polymer of glucose. The dialysate is subjected to crossflow filtration to generate a retentate that includes all or a portion of the amount of osmotic agent, along with amounts of other components of the dialysate. The filtration also generates a permeate that includes amounts of other components of the dialysate.

Embodiments of the methods and systems disclosed herein can utilize any of a variety of PD fluids, including in some forms high molecular weight (HMW) PD fluids. An example is Icodextrin, a high molecular weight starch dissolved in water. In particular, Icodextrin is a starch-derived, branched, water-soluble glucose polymer linked by α-(1→4) and less than 10% α-(1→6) glycosidic bonds. Its weight-average molecular weight is between 13,000 and 19,000 Daltons. Icodextrin is manufactured by Baxter Healthcare Corporation (sold under the tradename Extraneal, containing about 7-8% by weight Icodextrin in aqueous solution) and is commonly used in current clinical practice. Icodextrin acts as a colloidal osmotic agent, although other high molecular weight osmotic agents can act as soluble, non-colloidal osmotic agents, and can also be used. Illustrative high molecular weight osmotic agents include glucose polymers (e.g. Icodextrin), polypeptides (including for example albumin), dextran, gelatin and polycations. These or other high molecular weight osmotic agents typically have a weight average molecular weight of at least 10,000 Daltons, for example usually in the range of about 10,000 to about 350,000 Daltons and often in the range of about 10,000 to about 30,000 Daltons.

The PD fluid will typically include water, the osmotic agent(s), electrolytes such as sodium, calcium, potassium and/or magnesium, and a buffer. The buffer can for example be a lactate buffer, acetate buffer, or bicarbonate buffer. Other ingredients may also be present. The PD fluid will typically have a physiologically acceptable pH, for example in the range of about 5 to about 8. The PD fluid will also typically have an osmolality in the range of about 270 to 450 milliosmoles (mOsm), and more typically about 280 to about 350 mOsm. The osmotic agent can be present at any suitable concentration, and in some embodiments is present in the PD fluid or solution at a concentration of about 3 to about 20% by weight, or about 5 to about 15% by weight.

When a hyper osmolar PD fluid such as Icodextrin is introduced into the peritoneal space, water is drawn from the blood into the fluid until equilibrium is achieved. At the same time, nitrogen containing waste products of metabolism diffuse into the PD fluid. This mixture is referred to as an ultrafiltrate and contains urea, creatinine and a group of incompletely identified molecules of intermediate size.

Embodiments of the presently disclosed methods and systems can employ the crossflow filtration step, alone or in combination with other steps, to recover and recycle the PD fluid and return it to the peritoneal space. At the same time, the process yields a concentrated ultrafiltrate, separated from most or all of the osmotic agent component, with the concentrated ultrafiltrate containing urea, creatinine and potentially other waste products that can be discarded.

FIG. 1 is a schematic representation of the structure and function of one embodiment of a PD fluid reconstitution apparatus. On the right side of FIG. 1 is a representation of the body of a patient and the peritoneal space 4 is shown into which uptake 2 and return 3 segments of a PD catheter have been placed. In some implementations, all of the components of the system, with the exception of the PD catheter, are contained within an apparatus 1 located outside of the patient, and in some forms worn by the patient. Thus, apparatus 1 can have a housing that houses the components of the system 1, with the exception of the PD catheter. The distal segments of the uptake and return lumens of the PD catheter are ideally positioned at locations within the peritoneal space that are distant from each other. In this example, the uptake lumen is a curl shape and is located in the cul-de-sac of the pelvis and the distal segment of the return lumen is straight and located in Morrison's pouch under the free margin of the liver. Other arrangements are also contemplated.

Dialysate fluid from the peritoneal space is transported through an uptake lumen of the PD catheter by the action of a pump 7. Optionally, the fluid initially passes through a preliminary filter 6, which removes particulate material, such as precipitated fibrin. In some implementations, it may be desirable for the filter 6 to have an average pore size to achieve a molecular weight cutoff (MWCO) of from about 100 to about 150 kDa. Filters of a variety of materials with such a MWCO are widely available (e.g., Millipore). In certain embodiments, the initial filter 6 or "prefilter" is designed to be easily replaceable once the function has been degraded by retained debris. The initial filter 6 can be arranged to filter out precipitated fibrin or mucoid materials from the dialysate fluid being removed from the peritoneal space, which materials may clog or otherwise degrade the performance of subsequent filters in the system. Optionally also, the used dialysate fluid from the peritoneal space can be processed to at least partially remove one or more components of the dialysate fluid prior to its being passed into filter chamber 8 as discussed below. It is nonetheless expected in most implementations that the used dialysate fluid processed by filter chamber 8 will contain the majority, substantially all (e.g. at least 90, or at least 95%), or all of the osmotic agent initially present upon withdrawal of the fluid from the peritoneal space, along with amounts of other components (e.g. electrolytes and metabolic waste products) processed through filter chamber 8 as discussed below.

In these or other embodiments herein, the pump (e.g. pump 7) can be any suitable pump, including for example an electrically powered pump such as peristaltic pump, a diaphragm pump, or a piston pump. In certain embodiments, the pump is powered by a brushless electric motor. In these or other motor driven pumps used herein, the it is preferred that the motor has the capacity to operate on a current draw of 2 amps or less while providing the pressures and flow rates desired for the PD process, including for example those preferred pressures and flow rates specified herein. The pump also desirably exhibits the capacity to operate on a voltage in the range of about 6 to about 24 volts. In some implementations, pump 7 or other pumps herein can be provided by a MG1000 Series Brushless Micropump, commercially available from TCS Micropumps Limited, United Kingdom, and in one specific illustration the pump can be provided by the MG1000F Brushless Micropump from TCS Micropumps.

In the illustrated embodiment, after passing through the pre-filtration provided by filter 6, the dialysate fluid passes into the high pressure side 9 of the first reverse osmotic filtration chamber 8. Here, the dialysate fluid comes into contact with the membrane 11. This membrane 11 desirably contains pores which achieve a molecular weight cut off that is lower than the weight average molecular weight of the osmotic agent (e.g. Icodextrin or other polymer of glucose) of the PD fluid. In the case of Icodextrin, the osmotic component has starch molecules with a range of molecular weights, and has a weight average molecular weight of about 13 kDa to 19 kDa. The membrane 11 may be made of one or more of a variety of commercially available materials, including, for example, cellulose, polysulfone, and polyethersulfone.

The action of the pump 7 generates sufficient pressure on the high pressure side of the first chamber so as to result in transit of some of the water and solute molecules which are below the MWCO across the membrane (forming a permeate) while the osmotic agent component of the dialysate is constrained by the membrane to the high pressure side (in a retentate). The water and small molecules which do cross the membrane 11 into the low pressure side 10 leave the first filtration chamber through low pressure efferent lumen 13 in the permeate. Since this is not dead end filtration, most of the fluid, including most or all of the osmotic component, leaves the high pressure segment of the first chamber through the high pressure efferent lumen 12 in the retentate. In some embodiments, in order to maintain the necessary pressure in the first filtration chamber 8, an adjustable outflow restriction 14, such as an adjustable valve, is placed in the fluid path. The contents of the retentate, or a fraction thereof, can be returned to the peritoneal space of the patient, potentially supplemented with additional materials or after further processing as discussed below. The contents of the permeate, or a fraction thereof (e.g. generated using operational components as discussed below), can be fed to a waste container 30, for example a bag worn by the patient.

The filter membrane 11 will typically have a pore size or molecular weight cutoff that is effective to generate a retentate that contains a predominant amount by weight (greater than 50% by weight) of the osmotic agent present in the used dialysate passed into the high pressure side 9 of the filter chamber 8. For these purposes the membrane will generally have a molecular weight cutoff that is lower than the weight average molecular weight of the osmotic agent, for example with the molecular weight cutoff for the filter membrane 11 being no greater than 90% of the weight average molecular weight of the osmotic agent. In some embodiments, including but not limited to those in which the osmotic agent is Icodextrin, the filter membrane 11 can have a molecular weight cutoff in the range of about 3 kilodaltons (kDa) to about 15 kDa, more preferably in the range of about 5 kDa to about 12 kDa, and on a particular embodiment about 10 kDa. In addition or alternatively, the filter membrane 11 can have a surface area of at least about 20 $cm^2$, or at least about 50 $cm^2$, for example typically in the range of about 20 $cm^2$ to about 1000 $cm^2$ and more typically in the range of about 50 $cm^2$ to about 500 $cm^2$. In these or other embodiments identified herein, the filter membrane 11 is beneficially a polyethersulfone filter membrane. The filter 8 can be provided, for example, by commercially available filter cartridges or other suitable filter devices. Illustratively, the first stage filter chamber 8 and its membrane 11 and other components can be provided by a crossflow ultrafiltration cassette, for example such as those available from Sartorius Stedim North America Inc. (Bohemia, N.Y., USA) under the tradename Vivaflow® (e.g. Vivaflow® 50, Vivaflow® 50R, or Vivaflow® 200). Flat sheet filter membranes or hollow fiber membranes can be used, with flat sheet membranes being preferred in some implementations. These and other filters and membranes enabling crossflow filtration, including crossflow ultrafiltration, to recover substantial amounts of the osmotic agent in the retentate, can be used.

Icodextrin and other polymeric osmotic agents in fresh (unused) or in used condition can be a mixture of polymer molecules with varying molecular weights, which together establish the weight average molecular weight of the osmotic agent. Filtration by membrane 11 can result in selective passage (to the permeate) of lower molecular weight polymer molecules as compared to higher molecular weight polymer molecules of such an osmotic agent, and thus the weight average molecular weight of the retentate exiting the high pressure side 9 of the filter chamber 8 can be higher than that of the used dialysate passed into the high pressure side 9 of the filter chamber 8. The elimination of the lower molecular weight polymer molecules by their passage to the permeate, and the exclusion of those lower molecular weight polymer molecules from the regenerated dialysate fluid returned to the peritoneal cavity, may decrease the incidence of absorption of the Icodextrin or other osmotic agent by the patient from the peritoneal cavity, as smaller molecules are often absorbed more readily than larger molecules. Where desired, however, any decrease in the weight average molecular weight of the osmotic agent caused by the filtering in chamber 8 can be reduced or eliminated by combining an additional amount of the same osmotic agent (e.g. a glucose polymer composition such as Icodextrin), except having a lower weight average molecular weight than that of the osmotic agent in the used dialysate, to the retentate of filter chamber 8 or a fraction thereof to be returned to the peritoneal space 4 of the patient. This additional amount of the same osmotic agent can, in some modes of practice, be added from electrolyte source 18 discussed further below.

The filtering in filter chamber 8 can in some embodiments cause an increase in the concentration of the osmotic agent in the retentate as compared to the used dialysate passing into the filter chamber 8, due to the relative retention of the osmotic agent by the membrane 11 and passage of water through the membrane 11. In some forms, the filtering in filter chamber 8 during a period of circulation of dialysate from and back to the peritoneal space 4 can be under conditions effective to cause a rate of increase in concentration of the osmotic agent in the dialysate in the peritoneal space 4 (in the absence of added liquid (e.g. water) or osmotic agent to the system 1 or peritoneal space 4) of at least about 0.5% per hour, at least about 1% per hour, or at least about 3% per hour, but typically not exceeding about 10% per hour. It will be understood, however, that this increase that is or would be caused by filtration through filter chamber 8 can optionally be reduced or eliminated by the addition of water or other physiologically compatible liquid to the retentate or fraction thereof prior to return to the peritoneal space 4 and/or by water from the patient's body transferred into the peritoneal space 4. In some forms, water can be added to such retentate or fraction thereof, where the water is recovered by processing the permeate from filter chamber 8 to recover water having reduced levels or no levels of urea, creatinine, and/or other metabolic wastes from the patient as compared to their concentration in the permeate resultant of filtering in filter chamber 8.

In some embodiments, the filter 8 is operated at a pressure in the range of about 15 pounds per square inch (psi) to about 100 psi (at the input to the high pressure side 9), more preferably in the range of about 20 psi to about 50 psi, and most preferably in the range of about 20 psi to about 30 psi. In addition or alternatively, the total used dialysate throughput through the filter chamber 8 will be in the range of about 20 ml/minute to about 300 ml/minute, or about 50 ml/minute to about 200 ml/minute; and/or the ratio of the permeate flow in ml/minute to the retentate flow in ml/minute exiting the filter chamber 8 will be in the range of about 1:50 to about 1:10, or in the range of about 1:40 to about 1:15, or in the range of about 1:35 to about 1:20.

In certain embodiments, the retentate and the permeate resulting from the filter 8 will have substantially equal (e.g. within 20% of one another, or within 10% of one another) concentrations of urea and creatinine, with the filter 8 thus not causing significant partitioning, or change in concentration, of these small molecules present in the spent dialysate removed from the peritoneal space of the patient. Nonetheless the creation of significant levels of permeate by the filter 8 will lead to the removal of significant amounts of urea, creatinine and potentially other wastes from the patient. In addition or alternatively, the retentate and the permeate resulting from the filter 8 can have substantially equal (e.g. within 20% of one another, or within 10% of one another) concentrations of sodium, magnesium, potassium, and/or calcium, and/or other electrolytes in the used dialysate withdrawn from the peritoneal space 4. While this may in some forms ultimately lead to some loss of these electrolyte(s), other components of the system can be provided to add amounts thereof to a regenerated dialysate to be returned to the peritoneal space 4 to partially or completely make up for the electrolyte(s) losses, and/or electrolytes can be administered (e.g. orally) to the patient to partially or completely make up for the electrolyte(s) losses. These and other variations will be apparent to those skilled in the field from the descriptions herein.

In preferred embodiments, the high pressure side 9 and the low pressure side 10 of filter chamber 8 are void space. Thus, all of the separation of components of the used dialysate caused by passage thereof into and out of the filter chamber 8 can be caused by the action of the membrane 11. This can facilitate beneficial flow of liquid through the filter chamber 8, and result in an unmodified retentate exiting filter chamber 8 through effluent tube 12 and an unmodified permeate exiting filter chamber through effluent tube 13.

However, in other embodiments, the high pressure side 9 and/or the low pressure side 10 can contain (e.g. be packed with) a particulate or other solid material that contacts and allows flow-through of liquid and that binds, selectively or non-selectively, one or more of anions, cations, waste, or other components of the liquid passing through the high pressure side 9 or low pressure side 10, respectively. Thus, this particulate or other solid material can modify the composition of the permeate or retentate generated by membrane 11 and thus provide a modified retentate and/or modified permeate that exits the filter chamber 8 through tube 12 and/or tube 13, respectively.

In various embodiments, peritoneal dialysis (PD) systems disclosed herein provide recapture and reconstitution of a high molecular weight (HMW) PD fluid. That fluid is then returned to the peritoneal space where it can act to draw additional waste metabolites and water into the peritoneal space.

Certain embodiments of the PD system 1 are small enough to be worn by or implanted in the patient, and/or may allow continuous operation 24 hours per day. In certain embodiments, continuous operation is facilitated by a compact battery that is also small enough to be worn. In other embodiments, a semi-continuous operation can be implemented. In such operations, PD fluid can be allowed a dwell time in the peritoneal space of the patient, during which no PD fluid is withdrawn from the peritoneal space by the PD system (e.g. with the pump or pumps of the PD system de-energized or off during the dwell time. After the dwell time, the PD system is operated (e.g. by energizing or turning on a pump or the pumps of the PD system) to withdraw amounts of the used or spent PD fluid from the patient's peritoneal space, process the PD fluid to form a regenerated fluid as disclosed herein, and return the regenerated fluid to the peritoneal space of the patient. The withdrawal and return of these fluids from the peritoneal space can be simultaneous, e.g. operated in a continuous fluid loop from and to the peritoneal space. In embodiments operated in a cyclic or semi-continuous manner, the dwell time can range from about 1 hour to about 12 hours, from about 2 hours to about 6 hours, or from about 3 hours to about 4 hours. In addition or alternatively, the time over which the PD system is operated to withdraw and return fluids to the patient can range from about 1 hour to about 12 hours, from about 2 hours to about 6 hours, or from about 3 hours to about 4 hours. Also, whether operated in continuous, semi-continuous or other modes, it certain embodiments, the PD system and methods generate a liquid volume exchange in the peritoneal space of at least about 8 liters per day, or at least 10 liters per day, and typically in the range of about 8 to 20 liters per day or about 10 to 15 liters per day.

Certain embodiments operate with PD catheters that are, or are similar to, catheters that are already in common use. Most commonly used PD catheters comprise a soft silicone material with a single lumen and multiple side holes located at a curved or straight distal segment. Certain embodiments of PD systems disclosed herein operate with a dual lumen PD catheter, with one lumen for uptake from the peritoneal space and a second lumen for returning reconstituted fluid to the peritoneal space. Such catheters, while not in common clinical practice have been previously well described.

In certain embodiments, also present is a recharging port for new PD fluid. The charging port can be located at any suitable position fluidly connecting to the fluid circuit in the PD system. One suitable location is shown as charging port 5 in FIG. 1. The osmotic agent does not remain permanently in the peritoneal space. Although the system is designed to reconstitute rather than discard the PD fluid, some loss of the starch molecules into the lymphatic system occurs in normal function of the peritoneal membrane. The half-life of the Icodextrin starch is between 12 and 18 hours. Therefore, in some implementations, at least 1 liter, for example 1-3 liters, of Icodextrin can be replenished on a daily basis.

The system 1 also preferably includes a battery 19 for electrically energizing pump 7. The system 1 also in preferred embodiments includes a controller 20 for controlling the operation of system components including for example the pump and the valve or other similar devices providing restrictor 14, when present. Controller 20 can be provided by dedicated electrical circuitry and/or can be software-implemented using a microprocessor as controller 20. Controller 20 is electrically energized by a battery 21, which can be the same battery powering pump 7 or can be a separate battery. In some embodiments, the battery or batteries energizing pump 7 and controller 20, can be housed in the same system 1 housing along with pump 7, filter 8, controller 20, and potentially also filter 6. The battery or batteries can use any suitable battery chemistry, including for example lead-acid, nickel-cadmium, lithium-based, or other battery chemistries. As well, the battery or batteries can be rechargeable, and the system 1 can include a charging input, for example a charging port, by which the battery or batteries can be recharged as necessary using wired or wireless charging systems fed by an external electrical power source, and/or through which the pump(s) or other electrically energizable components of the system can be energized while the system 1 is connected to the external electrical power source. As well, in preferred systems 1, the speed of pump 7 is variable, and a control input (for example a knob or touch display input) is provided in the system 1 for varying the speed of pump 7. In this manner, the patient and/or a health care provider can locally adjust the speed of pump 7 to alter the filtration conditions within filter chamber 8.

As discussed above, processing through filter 8 may result in some loss of osmotic agent, electrolytes or minerals such as calcium, magnesium, sodium and/or potassium, and/or buffering solutes such as lactate, acetate or bicarbonate, from the dialysate withdrawn from the peritoneal space 4. In one mode, to partially or completely make up for the loss(es), an aqueous electrolyte source 18 can be provided, and the aqueous electrolyte solution thereof can be metered into or otherwise combined with the retentate in tube 12 for return to the peritoneal space of the patient, controlled for example by valve 18A positioned between source 18 and tube 12 that can be selectively opened or closed, and/or potentially also adjusted to various flow restriction levels. Valve 18A can in some forms be controlled by controller 20. Thus, this electrolyte source can include one, some or all of an osmotic agent (e.g. any one of those taught herein, which can be the same as or different from the osmotic agent in the dialysate withdrawn from the peritoneal cavity), calcium, magnesium, sodium and potassium, and potentially also other electrolytes, minerals, nutrients, and/or possibly also therapeutic agents. It will be understood that the electrolyte solution of source 18 can be more concentrated in the electrolytes and/or other solute(s) than is desired for return to the peritoneal space, but that the added amounts of this electrolyte solution will be diluted into the liquid in line 12. In this mode of operation, advantageously, relatively low volumes of electrolyte solution from source 18 can be added (due to its concentrated nature). This can aide, for example, in minimizing the weight that must be supported by the patient when the source 18 is to be carried by the patient (e.g. as connected to or contained within the system 1 housing). It will be appreciated that in preferred embodiments, the source 18 will be configured to meter its solution into the liquid stream in tube 12, for example powered by an electric pump which in turn can be energized by a battery. This pump and battery can be the same as that or different from those powering fluid flow (e.g. pump 7) or electrically energizing (e.g. battery 19) other components of the system 1.

In some embodiments, the entire retentate from filter 8 exiting through tube 12 can be returned to the peritoneal space 4 of the patient, either alone or after combination with one or more additional components. In other embodiments, the retentate from filter 8 may be further processed through one or more operational components 15 before returning a fraction thereof to the peritoneal space 4. Illustratively, in some modes of operation, the retentate can be subjected to further membrane and/or other filtration before returning a fraction of the retentate to the peritoneal space 4, while in other embodiments, the retentate, or a fraction thereof, can be returned to the patient without having subjected the retentate to further membrane and/or other filtration. Additionally or alternatively, the retentate can be subjected to still other types of separation processing to separate a fraction thereof, before returning that fraction of the retentate to the peritoneal space. These other separation processing techniques may include, for example, passing the retentate or fractions thereof over sorbents, ion-exchange resins, or other solids to separate materials to be returned to the peritoneal space 4 (e.g. amounts of electrolyte species such as cations, e.g. sodium, potassium, magnesium and/or calcium) from materials to be discarded into waste container 30 (e.g. amounts of urea, creatinine and/or other metabolic wastes of the patient), for example through tube 15A.

In addition to or as alternatives to the above-discussed embodiments regarding processing of the retentate from filter 8, in some embodiments, the entire permeate from filter 8 can be passed to discard container 30 and thus no fraction of the permeate returned to the peritoneal space 4. In other embodiments, the permeate from filter 8 may be further processed through an additional operational component stage 16, and one or more fractions generated thereby can be returned to the peritoneal space 4, for example passing through tube 17A and/or tube 17B and combining with the retentate from filter 8 or a fraction thereof in tube 12 prior to return to the peritoneal space 4. Illustratively, in some modes of operation, at operational component stage 16, the permeate can be subjected to further membrane filtration, for example nanofiltration and/or reverse osmosis filtration, before returning a fraction of the retentate (e.g. including recovered water) to the peritoneal space 4, while in other modes of operation, a fraction of the permeate from filter chamber 8 can be returned to the patient without having subjected the permeate to nanofiltration and/or reverse osmosis filtration. Additionally or alternatively, the permeate from filter chamber 8 can be subjected to other types of separation processing at operational component stage 16 to separate a fraction thereof, before returning that fraction of the permeate to the peritoneal space. These other separation processing techniques may include, for example, passing the permeate or fractions thereof over sorbents, ion-exchange resins, or other solids to separate materials to be returned to the peritoneal space 4 (e.g. amounts of electrolyte species such as cations, e.g. sodium, potassium, magnesium and/or calcium) from materials to be discarded (e.g. amounts of urea, creatinine and/or other metabolic wastes of the patient). Where first and second sub-stage separations are conducted in operational component stage 16 to generate separate fractions to be returned to the peritoneal space 4, it can be beneficial sometimes to include both tubes 17A and 17B so that the fractions can be separately combined with the retentate from filter chamber 8 or a fraction thereof in tube 12 at separate locations (e.g. before or after operational component stage 15, when present). In other embodiments, only one of tubes 17A and 17B need be present to combine the fraction or fractions generated by operational component stage 16 with the contents of tube 12.

When both operational component stages 15 and 16 are included in the system 1, in some embodiments, the output from operational component stage 16 to be returned to the peritoneal space 4 can be combined with the retentate from filter chamber 8 (exiting chamber 8 through tube 12) before such retentate is subjected to operational component stage 15 (e.g. passing through tube 17A). In other embodiments including operational component stages 15 and 16, the output from operational component stage 16 to be returned to the peritoneal space 4 can be combined with a fraction of the retentate from filter chamber 8 to be returned to the peritoneal space 4 (e.g. through tube 17B), with such fraction of the retentate from filter chamber 8 having been generated by operational component stage 15. It will be understood that where operational component stage 16 is included, it will not be necessary in all embodiments to include both tubes 17A and 17B—one or the other can be included. In other embodiments where operational component stage 16 is included, both tubes 17A and 17B can be included. These and other variations will be apparent to those skilled in the field from the descriptions herein.

Systems 1 are desirably relatively lightweight and wearable or otherwise portable by the patient. In certain embodiments, the weight of the system 1 housing and the components within the system 1 housing, will be less than 5 kg, more preferably less than 3 kg, and even more preferably less than 2 kg. For wearable systems 1, the housing and its components can be supported on the patient by a belt, harness, backpack, or any other suitable attachment member that can be worn around or over a body portion of the patient. As well, other wearable systems with these or other attachment members may have one or more than one housings or other support structures (typically rigid metal and/or plastic structures), that house or support different ones of the components of systems 1.

Additionally, where systems 1 include a housing that houses components of the system 1, the housing can in some forms be segmented to provide at least a first compartment and a second compartment, each housing separate component(s) of the system. For example, the first compartment can be manually accessible by the patient or by a caregiver, and can contain components that are to be periodically replaced, for example in some embodiments the filter 6, the filter chamber 8, the operational component 15, the operational component 16, the electrolyte source 18, and/or inputs to adjust the speed of pump 7 and/or the adjustable restrictor 14. The second chamber, on the other hand, can contain system components that are not expected to be accessed by the caregiver or patient, for example the pump 7, the battery or batteries 19 and 21, and/or the controller 20. Thus, the second chamber can be sealed or otherwise closed to access except with the aid of a tool or tools.

Listing of Certain Embodiments

The following provides a non-limiting listing of embodiments disclosed herein:

Embodiment 1. A method for processing a used peritoneal dialysate recovered from a peritoneal space of a patient, the used peritoneal dialysate containing an osmotic agent, urea, creatinine, and sodium, method comprising:
  filtering the used dialysate under crossflow filtration conditions across a membrane having a molecular weight cutoff lower than a weight average molecular weight of the osmotic agent, said filtering generating:
    a retentate containing at least 50% by weight of the osmotic agent present in the used dialysate, a first concentration of urea from the used dialysate, a first concentration of creatinine from the used dialysate, and a first concentration of sodium from the used dialysate; and
    a permeate containing a second concentration of urea from the used dialysate, a second concentration of creatinine from the used dialysate, and a second concentration of sodium from the used dialysate.

Embodiment 2. The method of embodiment 1, wherein:
  said osmotic agent has a weight average molecular weight in the range of about 10 kDa to about 30 kDa.

Embodiment 3. The method of embodiment 1 or embodiment 2, wherein: said molecular weight cutoff is in the range of about 3 kDa to about 15 kDa.

Embodiment 4. The method of any one of the previous embodiments, wherein: said osmotic agent comprises a polymer of glucose.

Embodiment 5. The method of any one of the previous embodiments, wherein: said osmotic agent comprises Icodextrin.

Embodiment 6. The method of any one of the previous embodiments, wherein:
  said filtering includes maintaining a high pressure side of said membrane and a low pressure side of said membrane, with the used dialysate being introduced to the high pressure side of said membrane; and
  the high pressure side of said membrane is maintained at a pressure in the range of about 20 to about 100 psi.

Embodiment 7. The method of embodiment 6, wherein said pressure is in the range of about 15 to about 100 psi.

Embodiment 8. The method of embodiment 7, wherein said pressure is in the range of about 20 to about 50 psi.

Embodiment 9. The method of any previous embodiment, wherein the membrane has a molecular weight cutoff not greater than 90% of the weight average molecular weight of the osmotic agent.

Embodiment 10. The method of embodiment 9, wherein the membrane comprises a polyethersulfone polymer membrane.

Embodiment 11. The method of any one of the previous embodiments, wherein:
  the first and second concentrations of urea are within 20% of one another, and preferably within 10% of one another.

Embodiment 12. The method of any one of the previous embodiments, wherein: the first and second concentrations of creatinine are within 20% of one another, and preferably within 10% of one another.

Embodiment 13. The method of any one of the previous embodiments, wherein: the first and second concentrations of sodium are within 20% of one another, and preferably within 10% of one another.

Embodiment 14. The method of any one of the previous embodiments, also comprising:
  returning the retentate or a fraction of the retentate to the peritoneal space of the patient.

Embodiment 15. The method of any one of the previous embodiments, also comprising:
  adding sodium to the retentate.

Embodiment 16. The method of any one of the previous embodiments, also comprising:
  adding sodium, potassium, calcium, magnesium, lactate, acetate, and/or bicarbonate to the retentate.

Embodiment 17. The method of any one of the previous embodiments, also comprising:
  adding an amount of a replenishing osmotic agent having a weight average molecular weight of at least 10 kDa to the retentate or to a fraction of the retentate.

Embodiment 18. The method of embodiment 17, wherein the replenishing osmotic agent is the same as the osmotic agent contained in the retentate or fraction of the retentate.

Embodiment 19. The method of embodiment 17, wherein the replenishing osmotic agent is different from the osmotic agent in the retentate or fraction of the retentate.

Embodiment 20. The method of embodiment 19, wherein the replenishing osmotic agent contains a replenishing polymeric osmotic agent that is the same as a polymeric osmotic agent in the retentate or fraction of the retentate, except that the replenishing polymeric agent has a weight average molecular weight that differs from that of the polymeric osmotic agent in the retentate or fraction of the retentate.

Embodiment 21. The method of embodiment 20, wherein the replenishing polymeric osmotic agent has a lower weight average molecular weight than that of the polymeric osmotic agent in the retentate or fraction of retentate.

Embodiment 22. The method of any one of the previous embodiments, also comprising:
discarding the permeate without returning the permeate or any fraction thereof to the peritoneal space of the patient; or
recovering a fraction of the permeate for return to the patient without having subjected the permeate to nanofiltration and/or reverse osmosis filtration.

Embodiment 23. The method of any one of the previous embodiments, wherein:
during the filtering, the membrane is housed in an apparatus being worn by the patient.

Embodiment 24. The method of any one of the previous embodiments, comprising, prior to the filtering:
withdrawing the used dialysate from the peritoneal space of the patient through a catheter lumen.

Embodiment 25. The method of any one of the previous embodiments, comprising, after the filtering:
returning the retentate or a fraction of the retentate to the peritoneal space of the patient through a catheter lumen.

Embodiment 26. The method of embodiment 25, also comprising, prior to the returning:
adding at least one of sodium, potassium, calcium, magnesium, lactate, acetate, bicarbonate, and/or a replenishing osmotic agent to the retentate.

Embodiment 27. The method of embodiment 26, wherein the replenishing osmotic agent comprises a polymer of glucose.

Embodiment 28. The method of embodiment 27, wherein the replenishing osmotic agent comprises a colloidal osmotic agent.

Embodiment 29. The method of embodiment 27 or 28, wherein the replenishing osmotic agent comprises Icodextrin.

Embodiment 30. A system for processing a used peritoneal dialysate from a peritoneal space of a patient, the used peritoneal dialysate containing an osmotic agent, urea, creatinine, and sodium, system comprising:
a catheter lumen for withdrawal of the used peritoneal dialysate from the peritoneal space of the patient;
a crossflow filtration filter with a membrane having a molecular weight cutoff lower than a weight average molecular weight of the osmotic agent, said crossflow filtration filter arranged to generate from the used peritoneal dialysate:
a retentate containing at least 50% by weight of the osmotic agent present in the used dialysate, a first concentration of urea from the used dialysate, a first concentration of creatinine from the used dialysate, and a first concentration of sodium from the used dialysate; and
a permeate containing a second concentration of urea from the used dialysate, a second concentration of creatinine from the used dialysate, and a second concentration of sodium from the used dialysate; and
a catheter lumen for return of at least said retentate or a fraction thereof to the peritoneal space of the patient.

Embodiment 31. The system of embodiment 30, also comprising:
a wearable system housing that houses at least the crossflow filtration filter.

Embodiment 32. The system of embodiment 31, wherein:
said wearable system housing also houses at least one battery and at least one electric pump electrically connected to and energizable by the battery.

Embodiment 33. The system of any one of embodiments 30 to 32, wherein:
the crossflow filtration filter has a surface area the range of about 20 to about 1000 $cm^2$.

Embodiment 34. The system of any one of embodiments 30 to 33, wherein:
said membrane comprises a polyethersulfone polymer.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

References to approximations are made throughout this specification, such as by use of the terms "about" or "approximately." For each such reference, it is to be understood that, in some embodiments, the value, feature, or characteristic may be specified without approximation. For example, where qualifiers such as "about," "substantially," and "generally" are used, these terms include within their scope the qualified words in the absence of their qualifiers.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment, nor does any particular embodiment necessarily require all features disclosed.

The invention claimed is:

1. A method for processing a used peritoneal dialysate recovered from a peritoneal space of a patient, the used peritoneal dialysate containing a polymeric osmotic agent, urea, creatinine, and sodium, method comprising:
(i) allowing a peritoneal dialysis fluid to dwell in the peritoneal space of the patient for a dwell time of about 1 to about 12 hours so as to form a used dialysate, wherein no amount of the peritoneal dialysis fluid is withdrawn from the peritoneal space of the patient during said dwell time;
(ii) after said allowing, operating a pump of an apparatus worn by the patient to withdraw the used dialysate from the peritoneal space of the patient
(iii) filtering the used dialysate under crossflow filtration conditions across a membrane received in a filter chamber of said apparatus and having a molecular weight cutoff lower than a weight average molecular weight of the osmotic agent, said filtering conducted with a throughput of the used dialysate through the filter chamber of about 50 ml/minute to about 200 ml/minute, said filtering being powered by said pump, and said filtering generating:
a retentate containing at least 70% by weight of the osmotic agent present in the used dialysate, a first concentration of urea from the used dialysate, a first concentration of creatinine from the used dialysate, and a first concentration of sodium from the used dialysate; and a permeate containing a second concentration of urea from the used dialysate, a second concentration of creatinine from the used dialysate, and a second concentration of sodium from the used dialysate;

wherein said molecular weight cutoff is in the range of about 3 kDa to about 15 kDa;

wherein said filtering includes maintaining a high pressure side of said membrane and a low pressure side of said membrane, with the used dialysate being introduced to the high pressure side of said membrane, wherein the high pressure side of said membrane is maintained at a pressure in the range of about 15 psi to about 100 psi; and wherein said filtering generates a flow of the permeate and a flow of the retentate, wherein a ratio of the flow of the permeate to the flow of the retentate is in the range of about 1:40 to about 1:15;

(iv) forming a reconstituted peritoneal dialysate, said forming a reconstituted dialysate including adding an amount of a replenishing polymeric osmotic agent to the retentate or to a fraction of the retentate, wherein the replenishing polymeric osmotic agent is the same as the polymeric osmotic agent in the retentate or the fraction of the retentate but having a weight average molecular weight that is lower than that of the polymeric osmotic agent in the retentate or fraction of the retentate; and (v) introducing the reconstituted peritoneal dialysate into the peritoneal space of the patient.

2. The method of claim 1, wherein:
said osmotic agent in said used peritoneal dialysate has a weight average molecular weight in the range of about 10 kDa to about 30 kDa.

3. The method of claim 1, wherein:
the retentate, or a fraction thereof, is returned to the patient in said reconstituted peritoneal dialysate without having subjected the retentate to further membrane filtration.

4. The method of claim 1, wherein:
said osmotic agent comprises a polymer of glucose.

5. The method of claim 1, wherein:
said osmotic agent comprises Icodextrin.

6. The method of claim 1, wherein:
the ratio of the flow of permeate to the flow of retentate is in the range of about 1:35 to about 1:20.

7. The method of claim 6, wherein said pressure is in the range of about 20 psi to about 50 psi.

8. The method of claim 7, wherein said pressure is in the range of about 20 psi to about 30 psi.

9. The method of claim 1, wherein the membrane comprises a polyethersulfone polymer membrane.

10. The method of claim 1, wherein:
said forming a reconstituted peritoneal dialysate also includes adding sodium, potassium, calcium, magnesium, lactate, acetate, and/or bicarbonate to the retentate or to a fraction of the retentate.

11. The method of claim 1, wherein:
the replenishing osmotic agent has a weight average molecular weight of at least 10 kDa.

12. The method of claim 11, wherein the replenishing osmotic agent is a polymer of glucose.

13. The method of claim 1, also comprising:
discarding the permeate without returning the permeate or any fraction thereof to the peritoneal space of the patient; or recovering a fraction of the permeate for return to the patient without having subjected the permeate to nanofiltration and/or reverse osmosis filtration.

14. The method of claim 1, wherein:
said operating a pump withdraws the used dialysate from the peritoneal space of the patient through a catheter lumen.

15. The method of claim 1, wherein:
said introducing the reconstituted peritoneal dialysate includes passing the reconstituted peritoneal dialysate through a catheter lumen and into the peritoneal space of the patient.

16. The method of claim 1, wherein said dwell time is about 2 hours to about 6 hours.

17. The method of claim 1, wherein said operating a pump is for a duration of about 1 hour to about 12 hours.

18. The method of claim 16, wherein said operating a pump is for a duration of about 2 hours to about 6 hours.

19. The method of claim 17, conducted so as to generate a liquid volume exchange in the peritoneal space of the patient of about 8 to about 20 liters per day.

\* \* \* \* \*